United States Patent
Ueda et al.

(10) Patent No.: US 8,384,030 B2
(45) Date of Patent: Feb. 26, 2013

(54) METHOD AND APPARATUS FOR SETTING SAMPLE OBSERVATION CONDITION, AND METHOD AND APPARATUS FOR SAMPLE OBSERVATION

(75) Inventors: Kazuhiro Ueda, Hitachinaka (JP); Tatsuya Maeda, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 590 days.

(21) Appl. No.: 12/043,946

(22) Filed: Mar. 6, 2008

(65) Prior Publication Data

US 2008/0217532 A1 Sep. 11, 2008

(30) Foreign Application Priority Data

Mar. 7, 2007 (JP) ................................. 2007-057552

(51) Int. Cl.
*G01N 23/00* (2006.01)
(52) U.S. Cl. ........................... 250/307; 250/310; 345/10
(58) Field of Classification Search .................... 250/307
See application file for complete search history.

(56) References Cited

U.S. PATENT DOCUMENTS

| | | | | |
|---|---|---|---|---|
| 5,635,715 A * | 6/1997 | Le Gressus et al. | .......... | 250/307 |
| 6,326,618 B1 * | 12/2001 | Kane et al. | .......... | 250/307 |
| 6,366,688 B1 * | 4/2002 | Jun et al. | .......... | 382/145 |
| 6,627,888 B2 | 9/2003 | Yamaguchi et al. | | |
| 6,635,873 B1 | 10/2003 | Todokoro et al. | | |
| 6,909,092 B2 * | 6/2005 | Nagahama et al. | .............. | 850/10 |
| 6,946,656 B2 * | 9/2005 | Ezumi et al. | .......... | 850/11 |
| 7,019,294 B2 * | 3/2006 | Koyama et al. | ............ | 250/311 |
| 7,159,599 B2 * | 1/2007 | Verhaverbeke et al. | ...... | 134/109 |
| 7,187,345 B2 * | 3/2007 | Kobaru et al. | .......... | 345/10 |
| 2005/0190310 A1 * | 9/2005 | Koyama et al. | .......... | 349/5 |

FOREIGN PATENT DOCUMENTS

| | | |
|---|---|---|
| JP | 05-151927 A | 6/1993 |
| JP | 07-014537 A | 1/1995 |
| JP | 2000-200579 A | 7/2000 |
| JP | 2005-061998 A | 3/2005 |
| JP | 2005-164451 A | 6/2005 |
| JP | 2006-003370 A | 1/2006 |

* cited by examiner

OTHER PUBLICATIONS

Office Action issued Jan. 10, 2012, in Japanese Application No. 2007-057552.

*Primary Examiner* — Phillip A Johnston
(74) *Attorney, Agent, or Firm* — Miles and Stockbridge P.C.

(57) ABSTRACT

A method and apparatus for setting a sample observation condition and a method and apparatus for sample observation which allow sample observation by speedily and simply finding an optimum condition while suppressing damage to the sample are provided. The setting of a sample observation condition according to the present invention is realized by an electron beam apparatus acquiring a profile at a predetermined evaluation location of a sample under a reference observation condition, by a processing section judging whether or not the above described acquired profile is located within a predetermined setting range and setting an optimum observation condition to be used for sample observation based on this judgment result. More specifically, locations where the condition can be examined are registered beforehand first and then a jump is made to the corresponding location which is irradiated with an electron beam (hereinafter referred to as "predosing") at a low magnification, the surface of the sample is charged, enlarged to an observation magnification and secondary electron information on the target location is obtained. After that, secondary electron information is obtained at any time while performing predosing, it is successively judged from the information whether the pattern bottom part can be observed/measured or whether or not the sample is destroyed and an optimum observation condition is thereby found.

20 Claims, 6 Drawing Sheets

PIXEL POSITION
IN HORIZONTAL DIRECTION

FIG. 9

BRIGHTNESS DISTRIBUTION
OF BOTTOM PART

PIXEL POSITION
IN HORIZONTAL DIRECTION

FIG. 12

BRIGHTNESS DISTRIBUTION
OF BOTTOM PART

METHOD AND APPARATUS FOR SETTING SAMPLE OBSERVATION CONDITION, AND METHOD AND APPARATUS FOR SAMPLE OBSERVATION

BACKGROUND OF THE INVENTION

1. Field of the Invention

The present invention relates to a method and apparatus for setting a sample observation condition, and a method and apparatus for sample observation, and more particularly, to a method and apparatus suitable for observing and measuring dimensions of a minute part, for example, a semiconductor device.

2. Background Art

Semiconductor devices in recent years have processing accuracies of 0.1 µm or less, and perform shape observation and dimensional control using a charged particle apparatus (mainly scanning electron microscope) in dimensional control for performance evaluation.

Figure 1:
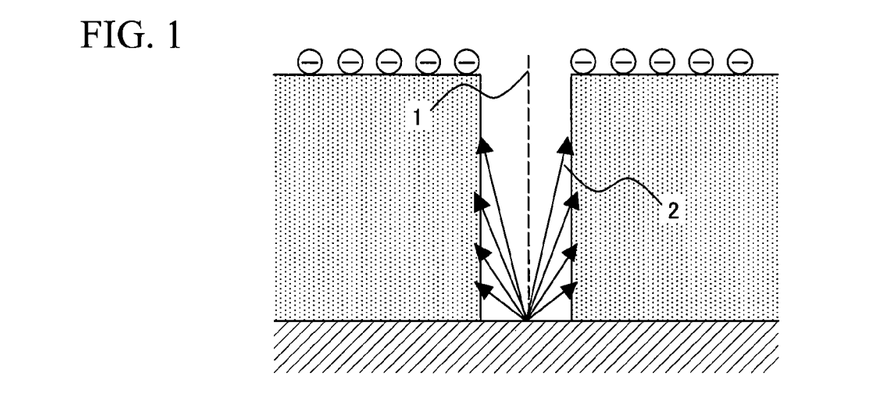
FIG. 1 is a principle diagram when secondary electrons at the bottom part cannot be detected in a pattern of a high aspect ratio.

In samples for those latest semiconductor devices, when the shape and size of a pattern with a high aspect ratio (having long depth in the ratio of the pattern size and depth) such as a contact hole are observed and measured, a secondary electronic signal 2 generated by scanning of an electron beam 1 at the bottom of the pattern having a high aspect ratio as shown in FIG. 1 may be interrupted by the sidewall of the pattern and unable to reach the surface of the sample, making it impossible to obtain necessary information and realize shape observation and size measurement.

Figure 2:
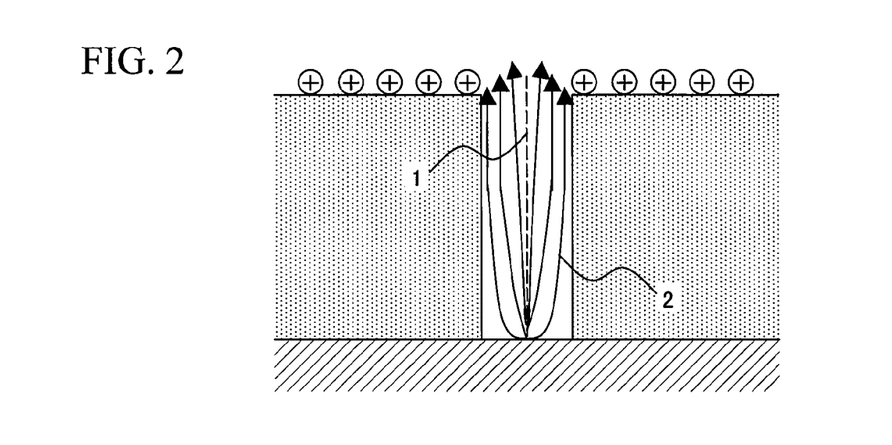
FIG. 2 is a principle diagram when detecting secondary electrons at the bottom part in a pattern of a high aspect ratio due to surface charge.

In order to solve such a problem, as shown in FIG. 2, for example, Patent Document 1 describes an art whereby a location to be evaluated is irradiated with an electron beam at a low accelerating voltage or a low magnification beforehand, the surface of the sample is (normally positively) charged (predosing), an electric field is formed between the bottom and the surface of the sample so that the secondary electronic signal 2 necessary for the shape observation and size measurement is made to reach the surface of the sample for detection.

[Patent Document 1] JP Patent Publication (Kokai) No. 2005-61998

SUMMARY OF THE INVENTION

Figure 3:
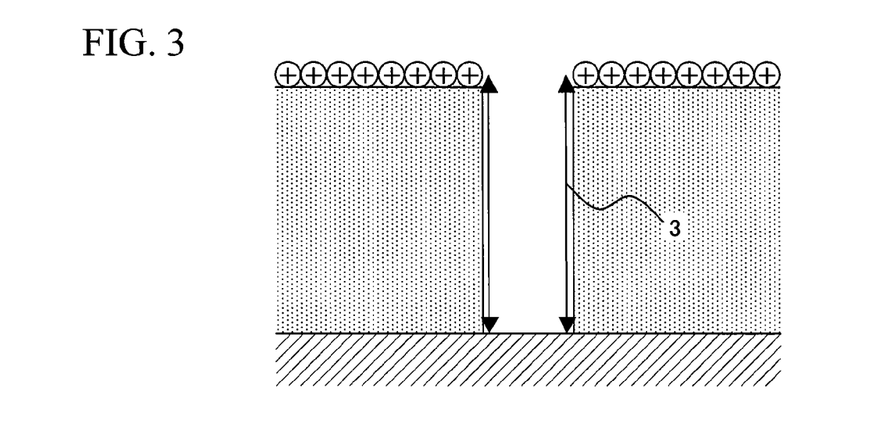
FIG. 3 is a principle diagram when discharge occurs on the surface of the sample and at the bottom part and dielectric breakdown occurs due to extreme surface charge in a pattern of a high aspect ratio.

However, since an optimum irradiation condition varies depending on the two-dimensional size and shape, material used and structure of the sample observed, simply applying predosing does not always solve the problem. Moreover, surface charging with excessive electron irradiation of a sample including an insulator in its structure produces an extreme potential difference between the surface of the sample and the pattern bottom as shown in FIG. 3, and therefore when the capacitance of the material used is exceeded, a discharge phenomenon 3 that the charge accumulated so far momentarily flows in a concentrated manner between the surface of the sample and the bottom, which may destroy the sample (dielectric breakdown). Therefore, it is difficult to find an optimum electron beam irradiation condition (observation condition: for example, magnification, accelerating voltage value and probe current value during predosing).

The present invention has been implemented in view of such circumstances, and provides a method and apparatus for setting sample observation conditions and a method and apparatus for sample observation which allow sample observation by speedily and simply finding an optimum condition while suppressing damage to the sample.

To solve the above described problems, the setting of a sample observation condition according to the present invention is realized by an electron beam apparatus acquiring a profile at a predetermined evaluation location of a sample under a reference observation condition, by a processing section judging whether or not the above described acquired profile is located within a predetermined setting range and setting an optimum observation condition to be used for sample observation based on this judgment result. Explaining the operation more specifically, in the present invention, locations where the condition can be examined are registered beforehand first and then a jump is made to the corresponding location which is irradiated with an electron beam (hereinafter referred to as "predosing") at a low magnification, the surface of the sample is charged, enlarged to an observation magnification and secondary electron information on the target location is obtained. After that, secondary electron information is obtained at any time while performing predosing, it is successively judged from the information whether the pattern bottom part can be observed/measured or whether or not the sample is destroyed and an optimum observation condition is thereby found.

In the operation of setting the optimum observation condition, if the profile is located within a predetermined setting range, the processing section employs the reference observation condition as an optimum observation condition, and if the profile is smaller than a lower limit of the predetermined setting range, the processing section changes the reference observation condition so as to increase the amount of surface charge of the sample, and if the profile is larger than an upper limit of the predetermined setting range, the processing section changes the reference observation condition so as to decrease the amount of surface charge of the sample. After the change, the evaluation location is moved to another location and a profile is acquired again using the changed observation condition. Furthermore, it may also be judged whether or not the electron beam apparatus can observe the sample under the changed observation condition and the processing may be finished if the electron beam apparatus cannot do so.

The sample includes the pattern of a high aspect ratio having a bottom part. In this case, a profile of the bottom part after predosing is acquired.

Further features of the present invention will be made clear with the preferred embodiments for implementing the present invention and the attached drawings below.

According to the present invention, it is possible to speedily and simply find an optimum observation condition for a sample while suppressing damage to the sample for which the conventional technique has difficulty in finding an optimum observation condition such as observation/measurement of a pattern bottom of a high aspect ratio of a semiconductor device.

DETAILED DESCRIPTION OF THE PREFERRED EMBODIMENTS

Hereinafter, an embodiment of the present invention will be explained with reference to the attached drawings. However, it should be noted that this embodiment is merely an example of implementing the present invention and not intended to limit the present invention. Furthermore, common configurations in the drawings are assigned the same reference numerals. In this embodiment, the present invention will be explained taking a scanning electron microscope as an example.

<Configuration of Scanning Electron Microscope>

Figure 4:
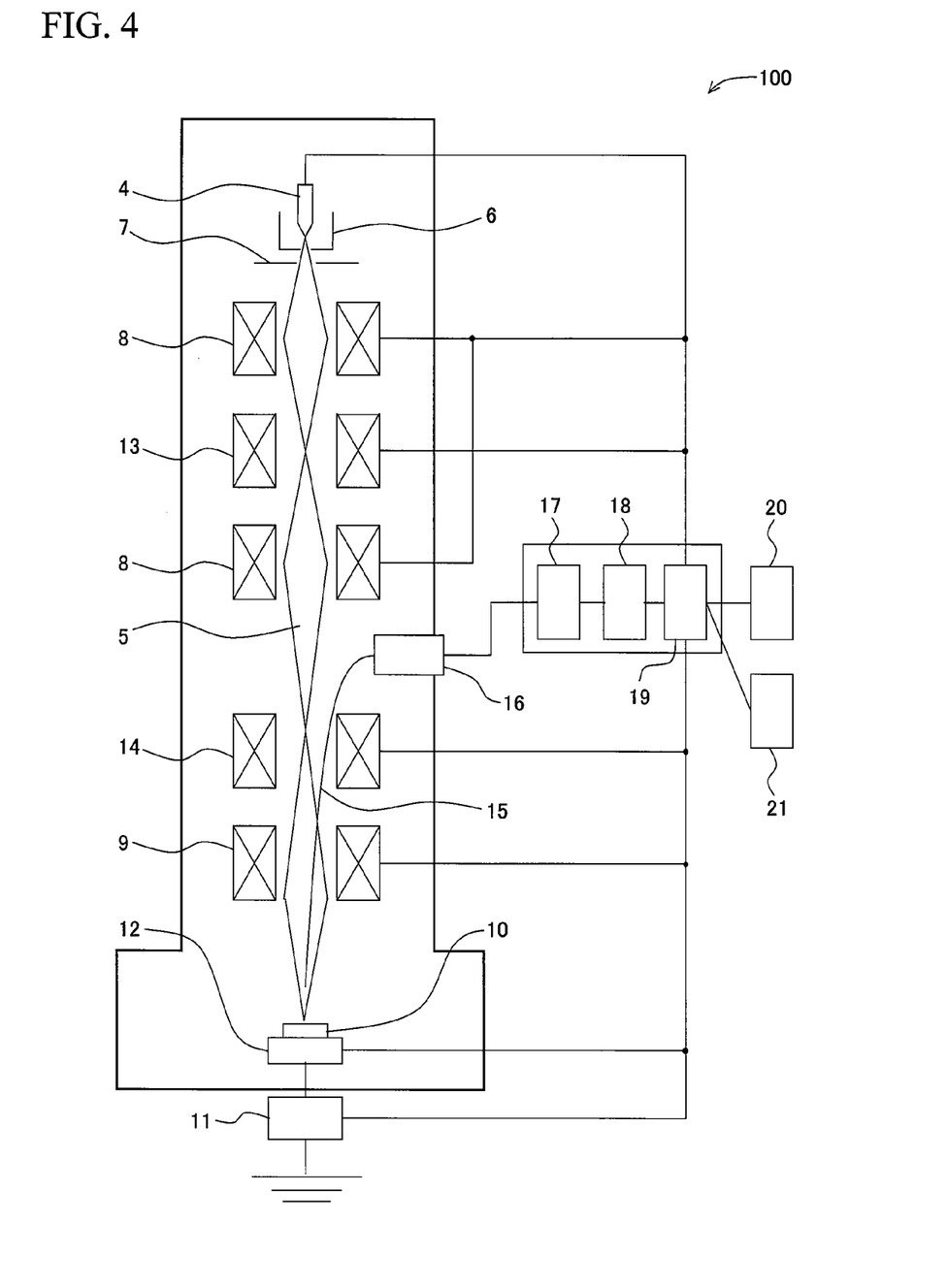
FIG. 4 shows a schematic configuration of an embodiment of the present invention using a scanning electron microscope.

FIG. 4 shows a schematic configuration of a scanning electron microscope 100 according to an embodiment of the present invention. In the scanning electron microscope 100, primary electrons 5 generated from a filament 4 which is an electron source are controlled and accelerated by a Wehnelt 6 and an anode 7. The Wehnelt 6 and anode 7 control an accelerating voltage which is the speed of irradiation onto the sample of the primary electrons 5 and a probe current which is the amount of current of irradiation onto the sample of the primary electrons 5. The accelerated primary electrons 5 are condensed to a sample 10 through a condenser lens 8 and an objective lens 9. A voltage generated by a sample voltage application apparatus 11 is applied to a stage 12 and the sample 10 and has the function of controlling the accelerating voltage of the primary electrons 5 when irradiated onto the sample 10.

The deviation of the primary electrons 5 from the center of the objective lens 9 and astigmatism of the primary electrons 5 are corrected by an alignment coil 13. Moreover, the primary electrons 5 are two-dimensionally deflected by a deflecting coil 14. Therefore, the sample 10 is also two-dimensionally scanned likewise. Secondary electrons 15, reflected electrons and X rays or the like are generated from the sample 10 scanned with the primary electrons 5 and among them, the secondary electrons 15, for example, are detected by a secondary electron detector 16 and converted to an electric signal.

This electric signal is introduced into an image storage device 17. Moreover, the scanned signal of the deflecting coil 14 is also introduced into the image storage device 17, and is stored in the image storage device 17 as the image of secondary electrons synchronized with the scanning with the primary electrons 5. The deflecting coil 14 controls the magnification by changing the scanning area on the sample 10.

As for the image of secondary electrons read from the image storage device 17, a place where a desired pattern exists is searched using a data calculation apparatus 18, the image of secondary electrons is then evaluated/measured and the result is stored a in data storage device 19. Since the technique of searching the place where the desired pattern exists is a well known technique, detailed explanations thereof will be omitted.

Furthermore, at an identical location of the sample 10, an image of secondary electrons is acquired while controlling the deflecting coil 14 and changing the magnification, and the degree of change before and after the irradiation with the electron beam is judged by the image storage device 17, data calculation apparatus 18 and data storage device 19. When a set value stored in the data storage device 19 and a set value inputted by an input device 21 or the like are satisfied, the processing is finished, whereas when the result is not satisfactory, the observation condition is changed, for example, by changing the probe current by controlling the filament 4, Wehnelt 6 and anode 7, by changing the accelerating voltage by controlling the sample voltage application apparatus 11 and by changing the magnification by controlling the deflecting coil 14. The deviation of alignment or the like produced when changing the observation condition is automatically corrected by controlling the alignment coil 13. Since this is a well known technique, detailed explanations thereof will be omitted.

Furthermore, the stage 12 is controlled based on information on the measuring location of the sample 10 stored in the data storage device 19 beforehand, the target is moved to a new location of the sample which has not been irradiated with the electron beam, an image of secondary electrons is acquired using a new observation condition and evaluated.

The above described operation is repeated until the condition registered beforehand is satisfied, and when the evaluation result is satisfactory or when the changed condition cannot be set or when all the registered measuring locations have been exhausted, the observation condition and the measurement result are stored in the data storage device 19 and/or outputted to a monitor 20 or the like and the processing is finished.

<Observation Condition Setting Processing Using Scanning Electron Microscope>

Figure 5:
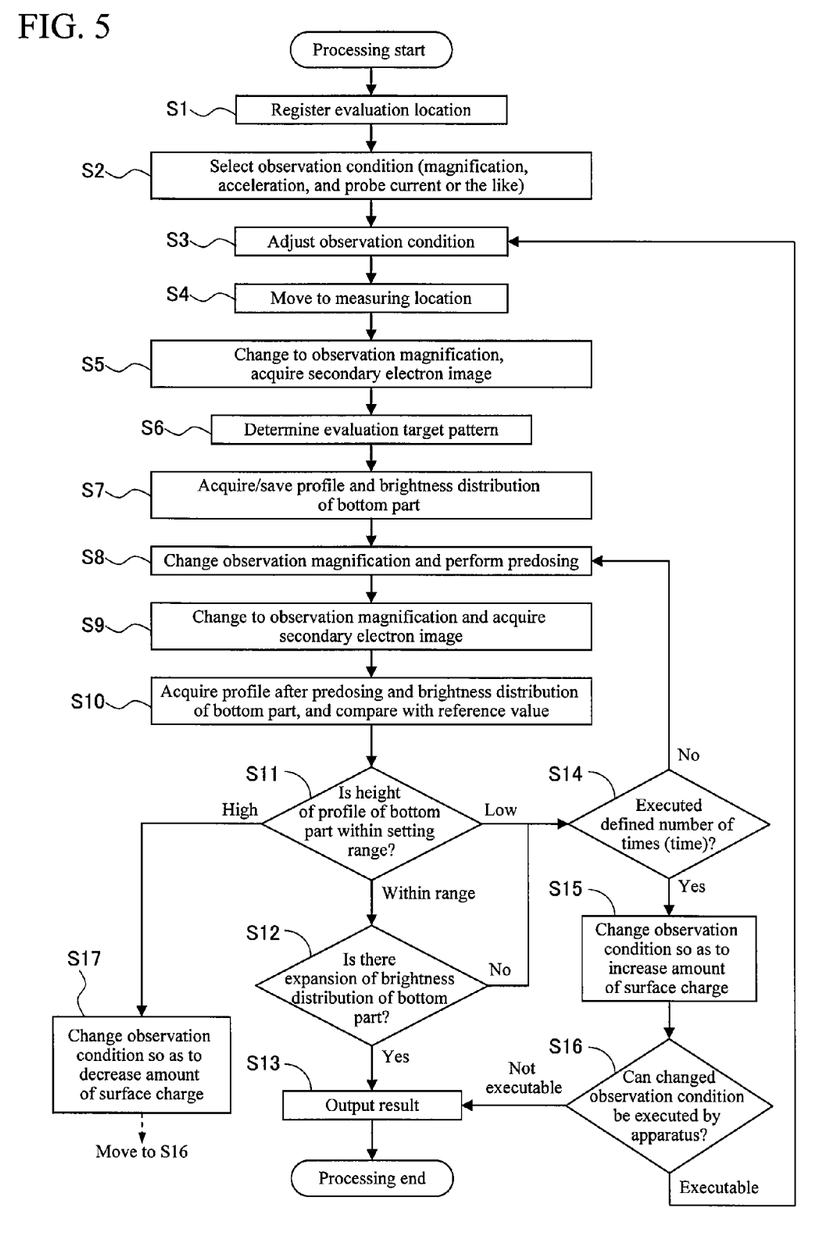
FIG. 5 is an example of flow chart for illustrating operation of an evaluation method (observation condition setting method) in the present invention.

FIG. 5 is a flow chart to explain the processing of setting the observation condition in the scanning type electron microscope shown in FIG. 4. In FIG. 5, the subject of processing control of each step is the data calculation apparatus 18 unless specified otherwise.

In step S1, evaluation locations (coordinate information) on the sample and images (templates) are registered (a plurality of locations). For example, a display prompting to input an evaluation location on the sample is shown on the monitor 20, the user specifies the coordinates of the evaluation location from the input device 21 such as a mouse or keyboard and the evaluation location is registered. Together with this, a display prompting to input an already known optimum condition (if any) is also shown. If a similar sample was observed in the past, the bottom part of the hole can be observed and the condition that does not cause destruction of the sample is already known in the judgment processing in steps S10 to S12 which will be described later (if the data was acquired before), the location can be immediately observed under the optimum condition by inputting the already known condition in step S1. Here, explanations will be continued assuming that the optimum condition is unknown.

In step S2, the observation condition such as an accelerating voltage, probe current and magnification are selected according to the input of the operator's instruction. The observation condition may also be automatically set to a default value. In step S3, the observation condition (acceleration current and probe current) is adjusted automatically or by prompting the user to adjust the condition based on the condition set in step S2. In step S4, the stage 12 is moved so that an electron beam is irradiated onto a measuring location based on information on the measuring point registered in step S1. In step S5, an image of secondary electrons is acquired at an observation magnification. In step S6, so-called pattern matching, that is, an image to be evaluated (pattern obtained in step S5) is decided by comparing the image with the image (template) inputted in step Si from among the acquired images. The processing from step S1 to step S6 is equal to the processing executed using the scanning electron microscope used for the dimensional control and observation or the like of semiconductor.

To confirm the shape of the bottom part which is the evaluation target in the present invention, intensity of secondary electrons (hereinafter referred to as a "profile") of the slope part (22 in FIG. 6) of the evaluation target, profile of the bottom part (23 in FIG. 6), and data of brightness (intensity) distribution of secondary electrons in the two-dimensional area of the bottom part enclosed by the slope part are acquired and saved in the image storage device 17 in step S7. Afterwards, in step S8, the surface of the sample is charged and the magnification is changed to a low magnification (1000× or the like) and predosing is performed so that a secondary electronic signal of the bottom part is obtained. In step S9, the magnification is returned to the observation magnification used in step S5 and an image of secondary electrons is acquired again. In step S10, a comparison is made between the reference value obtained in step S7, the profile of the slope part obtained in step S9, the profile of the bottom part and the data of brightness distribution. In other words, the comparison result is used for the judgment as to whether or not predosing has been effective.

When the shape of the bottom part 23 (see FIG. 6) approximates to an observable state through predosing, the amount of acquired secondary electrons in the bottom part increases and the height of the profile (signal intensity) increases. Thus, in step S11, the profile is judged. In other words, a comparison is made between the height of the profile of the slope part obtained in step S7, the height of the profile of the bottom part in an initial state, and the height of the profile of the bottom part acquired in step S9. When the set value is satisfied, the process moves to step S12, whereas when the set value is not satisfied, the process moves to step S14 or S17.

In the area of the bottom part enclosed by the slope part, if the shape becomes an observable state through predosing, the amount of acquired secondary electrons varies depending on the pattern shape and the brightness distribution is broadened. From this, in step S12, when the brightness distribution of secondary electrons in the bottom part after predosing is broadened compared to the brightness distribution of secondary electrons in the bottom part in the initial state, it is judged that the shape of the bottom part is observable. In step S13, the observation condition of predosing or the like is outputted and the processing is finished. The observation condition as this output is used when the same sample is mass-produced or the like later.

When the height of the profile of the bottom part acquired in step S11 is lower than the set value, the number of times (time) predosing is performed at the observation location is confirmed in step S14. If the number of times predosing is performed is smaller than the predetermined value inputted in step S1, the process returns to step S8 and predosing is performed. If predosing has already been performed the predetermined number of times (time) or more in step S14, a predosing condition such as an accelerating voltage, magnification and probe current is changed in step S15 so as to increase the effect of the surface charge. Afterwards, a judgment is made in step S16, and if the condition changed by the measuring apparatus is executable, the process returns to step S3 and the state of the apparatus such as axis adjustment is readjusted. Next, in step S4, at the observation location registered in step S1, the electron beam irradiation position is moved to a place where electron beam irradiation was never performed in the past and the process is repeated under a new observation condition. This is because since predosing has already been performed once at the same measuring location, processing under the accurate observation condition cannot be performed. In step S16, if the observation condition changed in step S15 is not executable (e.g., in the case of a physically unsettable accelerating voltage value and magnification), the observation conditions of predosing or the like acquired so far and/or the result that the observation conditions are not executable are/is outputted and the processing is finished.

In step S11, the height of the profile of the slope part and the height of the profile of the bottom part in an initial state are compared and when the height of the acquired profile of the bottom part is higher than the set value, that is, when the height of the profile of the bottom part becomes equivalent to that of the slope part, it is judged that there is a possibility of dielectric breakdown and the condition of predosing such as the accelerating voltage, magnification and probe current is changed so as to decrease the effect of the surface charge in step S17. Next, a judgment in step S16 is made and it is judged whether or not the changed condition is executable by the measuring apparatus. The processing thereafter is the same as that described above, and therefore explanations thereof will be omitted.

In this embodiment, a scanning electronic microscope is used as the measuring apparatus, but the present invention is also applicable to a transmission electron microscope or other apparatuses using electron beams. Furthermore, in this embodiment, the information detected from the sample is secondary electron information, but the information detected may also be obtained from an apparatus for charged particles such as reflected electrons or X rays. Furthermore, this embodiment has explained the image storage device 17, data calculation apparatus 18 and data storage device 19 as apparatuses independent of each other, but it goes without saying that these processes may also be performed by a program stored in a computer.

Examples

Figure 6:
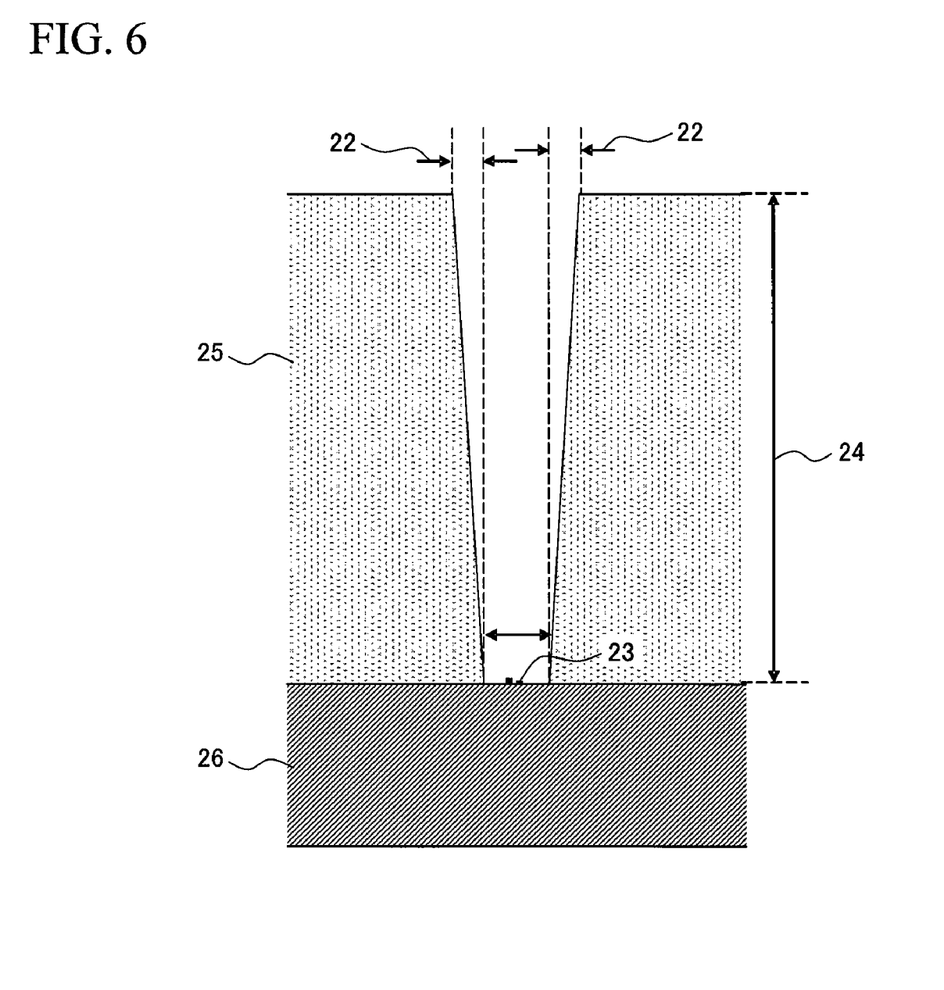
FIG. 6 is a cross-sectional view of an observation pattern according to Embodiment 1.

Examples using the measuring method according to the present invention will be explained using FIG. 6 to FIG. 12. FIG. 6 shows the structure of a sample in this embodiment. This sample has a deeper pattern depth 24 compared to the pattern size, that is, the widths of the slope part 22 and bottom part 23. Furthermore, the material of the pattern to be evaluated is $SiO_2$ 25 in the upper part and Si 26 in the lower part, and when the surface of $SiO_2$ 25 is extremely charged by predosing, there is a possibility that dielectric breakdown may occur.

Figure 7:
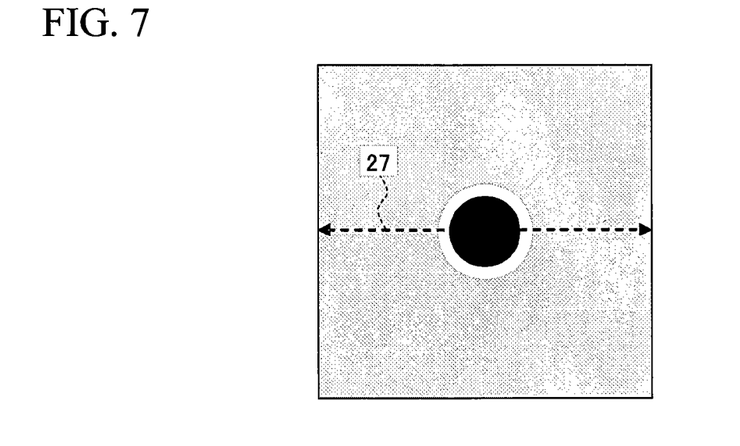
FIG. 7 shows an image of secondary electron acquired before predosing in the pattern in FIG. 6.
Figure 8:
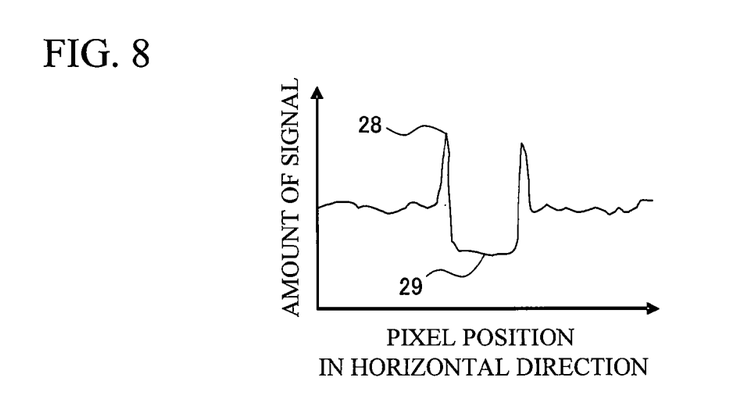
FIG. 8 shows a profile of secondary electrons at the central part of the evaluation target pattern in the X direction in FIG. 7.
Figure 9:
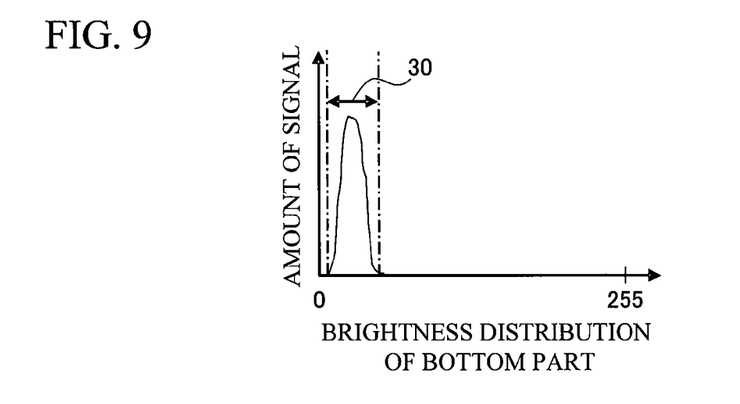
FIG. 9 shows a brightness distribution of secondary electrons at the bottom part of the evaluation target pattern in FIG. 7.

When the sample shown in FIG. 6 was evaluated according to the procedure in FIG. 5, the shape of the bottom part as shown in FIG. 7 could not be observed because the aspect ratio of the sample was high. In step S6, the pattern to be evaluated was searched from within the screen in FIG. 7, the profile at the central position 27 in the X direction shown in FIG. 8 was obtained and the heights of the peak portion 28 and bottom part 29 were stored. Furthermore, the brightness distribution of the bottom part enclosed by the peak portion was obtained as shown in FIG. 9 and the expansion of brightness 30 was stored.

Figure 10:
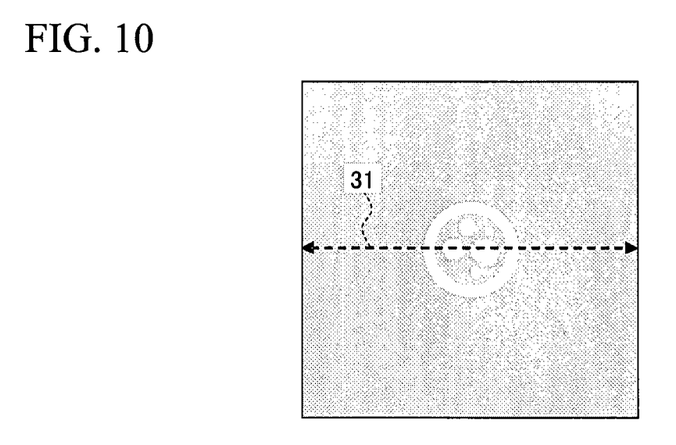
FIG. 10 shows an image of secondary electrons acquired after executing predosing in the pattern in FIG. 6.
Figure 11:
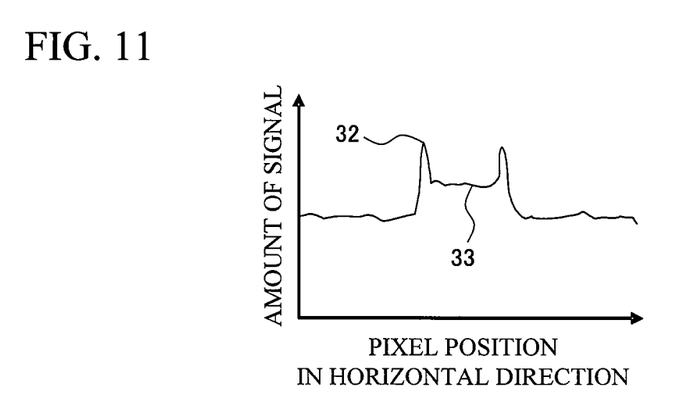
FIG. 11 shows a profile of secondary electrons at the central part of the evaluation target pattern in the X direction in FIG. 10.
Figure 12:
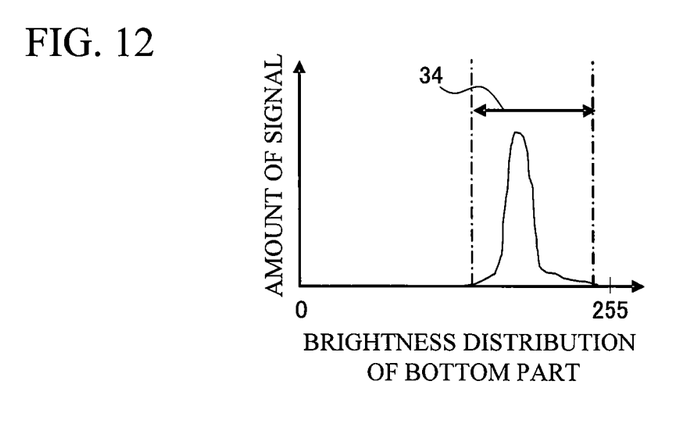
FIG. 12 shows a brightness distribution of secondary electrons at the bottom part of the evaluation target pattern in FIG. 10.

Afterwards, when predosing was performed and the image in step S9 was acquired, an image as shown in FIG. 10 was obtained. In step S10, a pattern to be evaluated was searched from within the screen in FIG. 10, the profile at the central position 31 in the X direction shown in FIG. 11 was obtained and the heights of the peak part 32 and bottom part 33 were stored. Furthermore, as shown in FIG. 9, the brightness distribution at the bottom part enclosed by the peak part was obtained and the expansion of brightness 34 was stored.

Furthermore, following step S11 in FIG. 5, a comparison was made with the height 29 of the bottom part in the initial state. Since the result showed that the height 33 of the profile at the bottom part after predosing increased, it was judged that a secondary electron signal was obtained from the bottom part. Furthermore, in the comparison between the height 33 of the profile of the bottom part after predosing and the height 32 of the profile of the slope part, the height 32 of the profile of the slope part was higher, and therefore it was judged that the observation condition would not cause dielectric breakdown and the process was moved to the next process.

Next, following step S12, a comparison was made with the expansion 30 of the brightness distribution at the bottom part in the initial state. Since the expansion 34 of the brightness distribution after predosing was greater, it was judged that the secondary electron signal obtained from the bottom part reflected the shape of the bottom part, that is, in an observable state, and the predosing condition such as magnification, the number of times (time) and probe current value was outputted following step S13 and the processing was finished.

In this embodiment, whether or not the secondary electron signal was obtained from the bottom part was judged based on the initial state 29 and the height of the profile after predosing 33, but a judgment may also be made by obtaining the ratio in height of the slope part and bottom part in the initial state (bottom part 29/slope part 28) and after predosing (bottom part 33/slope part 32) and comparing them.

Furthermore, this embodiment has explained the case where a contact hole is used as the sample, but the embodiment is also applicable to the shape of a line pattern or the like in which case the aspect ratio is high and the shape of the bottom is hard to judge through a normal observation.

Conclusion

In the sample observation condition setting according to this embodiment, the electron beam apparatus acquires a profile at a predetermined evaluation location of a sample under a reference observation condition first. Next, the processing section judges whether or not the above described acquired profile is located within a predetermined setting range and sets an optimal observation condition to be used for sample observation. This makes it possible to distinguish whether or not the first set observation condition is an optimum one, and when the first set observation condition is judged to be optimum, it is possible to observe the sample with certainty that the using the observation condition, the sample can be observed appropriately. On the other hand, when the first set observation condition is judged not to be optimum, it is possible to recognize that the observation condition should be changed.

Explaining the operation more specifically, a location at which the condition can be examined is registered first, a jump is made to the corresponding place, an electron beam is irradiated (hereinafter referred to as "predosing") at a low magnification, the surface of the sample is charged, the magnification is enlarged to an observation magnification and secondary electron information at the target location is obtained. Afterwards, secondary electron information is obtained as required while performing predosing, it is successively judged from the information whether the pattern bottom part is observable or measurable or whether or not the sample is destroyed, and an optimum observation condition is thereby found. That is, the optimum observation condition provides an observation condition whereby the pattern bottom part can be observed without destroying the sample (especially magnification of predosing). Therefore, using the observation condition obtained allows an image of the pattern bottom to be obtained with sufficient brightness without destroying the sample.

Furthermore, in the operation of setting an optimum observation condition, if the profile is located within a predetermined setting range, the processing section regards the reference observation condition as an optimum observation condition, and when the profile is lower than a lower limit of the predetermined setting range, the processing section changes the reference observation condition so as to increase the amount of surface charge of the sample and when the profile is larger than an upper limit of the predetermined setting range, the processing section changes the reference observation condition so as to decrease the amount of surface charge of the sample. After the change, the evaluation target is moved to another location and a profile is acquired again using the changed observation condition. Furthermore, it is judged whether or not the electron beam apparatus can observe the sample under the changed observation condition, and the processing may be finished when the electron beam apparatus cannot observe the sample. In this way, the observation condition is acquired adaptively, and it is thereby possible to find an observation condition speedily and simply while suppressing damage to the sample.

The present invention is applicable to the method and apparatus for sample measuring in an electronic microscope.

The present invention can also be implemented with a program code of software which realizes the functions of the embodiment. In this case, a storage medium in which the program code is recorded is supplied to a system or apparatus and the system or a computer of the apparatus (or CPU or MPU) reads the program code stored in the storage medium. In this case, the program code itself read from the storage medium realizes the functions of the aforementioned embodiment and the program code itself and the storage medium which stores the program code constitute the present invention. Examples of the storage medium which supplies such a program code include a floppy (registered trademark) disk, CD-ROM, DVD-ROM, hard disk, optical disk, magneto-optical disk, CD-R, magnetic tape, nonvolatile memory card and ROM.

Furthermore, the OS (operating system) operating on the computer or the like may execute part or the whole of the actual processing and realize the aforementioned functions of the embodiment through the processing. Furthermore, after the program code read from the recording medium is written into a memory in the computer, the CPU or the like of the computer may execute part or the whole of the actual processing based on instructions of the program code and realize the aforementioned functions of the embodiment through the processing.

Furthermore, a program code of software which realizes the functions of the embodiment may be delivered via a network, stored in a hard disk of the system or apparatus, storage means such as a memory or a storage medium such as CD-RW or CD-R, and the computer (or CPU or MPU) of the system or apparatus may read and execute the program code stored in the storage means or storage medium to thereby realize the functions of the embodiment.

What is claimed is:

1. A sample observation condition setting method for setting a sample observation condition in an electron beam apparatus, comprising:
    a first step, by the electron beam apparatus, of positively charging an evaluation location including a hole pattern of the sample by electron beam irradiation using a reference observation condition and subsequently acquiring a profile of the hole pattern of the sample;
    a second step, by a processing section, of determining if a signal amount of the profile corresponding to a bottom part of said hole pattern is within a predetermined range, which is selected to avoid dielectric breakdown due to the charging; and
    a third step, by the processing section, of setting an optimum observation condition for subsequent charging and profile acquisition by the electron beam apparatus based on a result of said determining,
    wherein the optimum observation condition includes a beam irradiation condition of the electron beam apparatus for charging the sample.

2. The sample observation condition setting method according to claim 1, wherein when said signal amount is within the predetermined range, said third step includes a step, by the processing section, of setting the reference observation condition as the optimum observation condition for the electron beam apparatus.

3. The sample observation condition setting method according to claim 1, wherein when said signal amount is less than the predetermined range, said third step includes:
    a step, by the processing section, of setting the optimum observation condition such that an amount of surface charge of the sample after irradiation by the electron beam apparatus using the beam irradiation condition of the optimum observation condition is increased as compared to a surface charge amount after irradiation by the electron beam apparatus using the reference observation condition in the first step.

4. The sample observation condition setting method according to claim 1, wherein when said signal amount is greater than the predetermined range, said third step includes:
    a step, by the processing section, of setting the optimum observation condition such that an amount of surface charge of the sample after irradiation by the electron beam apparatus using the beam irradiation condition of the optimum observation condition is decreased as compared to a surface charge amount after irradiation by the electron beam apparatus using the reference observation condition in the first step.

5. The sample observation condition setting method according to claim 3, further comprising, determining if the electron beam apparatus is capable of the optimum observation condition, and
    if the electron beam apparatus is determined to be capable of the optimum observation condition:
        moving to another evaluation location including a hole pattern of the sample; and
        repeating the first step at the another evaluation location using the optimum observation condition.

6. The sample observation condition setting method according to claim 4, further comprising determining if the electron beam apparatus is capable of the optimum observation condition, and
    if the electron beam apparatus is determined to be capable of the optimum observation condition:
        moving to another evaluation location including a hole pattern of the sample; and
        repeating the first step at the another evaluation location using the optimum observation condition.

7. The sample observation condition setting method according to claim 1, wherein the hole pattern has a high aspect ratio, and
    in said first step, a profile of the bottom part is acquired.

8. A sample observation method for observing a sample using the optimum observation condition obtained using the sample observation condition setting method according to claim 1.

9. A sample observation condition setting apparatus for setting a sample observation condition, comprising:
    an electron beam apparatus; and
    a processing apparatus,
    wherein the electron beam apparatus is constructed to positively charge an evaluation location including a hole pattern of a sample by electron beam irradiation using a reference observation condition and to acquire a profile of the hole pattern of the sample,
    the processing apparatus is configured to determine if a signal amount of the acquired profile corresponding to a bottom part of the hole pattern is within a predetermined range, which is selected to avoid dielectric breakdown due to charging by the electron beam apparatus,
    the processing apparatus is additionally configured to set an optimum observation condition for subsequent charging and profile acquisition by the electron beam apparatus based on a result of the determination, and
    the optimum observation condition includes a beam irradiation condition of the electron beam apparatus for charging the sample.

10. The sample observation condition setting apparatus according to claim 9, wherein the processing apparatus is configured to set the reference observation condition as the optimum observation condition for the electron beam apparatus when said signal amount is within the predetermined range.

11. The sample observation condition setting apparatus according to claim 9, wherein the processing apparatus is configured to set the optimum observation condition when said signal amount is less than the predetermined range such that an amount of surface charge of the sample after irradiation by the electron beam apparatus using the beam irradiation condition of the optimum observation condition is increased as compared to a surface charge amount after irradiation by the electron beam apparatus using the reference observation condition.

12. The sample observation condition setting apparatus according to claim 9, wherein the processing apparatus is configured to set the optimum observation condition when the signal amount is greater than the predetermined range such that an amount of surface charge of the sample after irradiation by the electron beam apparatus using the beam irradiation condition of the optimum observation condition is decreased as compared to a surface charge amount after irradiation by the electron beam apparatus using the reference observation condition.

13. The sample observation condition setting apparatus according to claim 11, wherein
the processing apparatus is further configured to determine if the electron beam apparatus is capable of the optimum observation condition, and
the electron beam apparatus is further configured to move to another evaluation location including a hole pattern of the sample, to charge the another evaluation location by electron beam irradiation using the optimum observation condition, and to acquire another profile at the another evaluation location when the processing apparatus determines that the electron beam apparatus is capable of the optimum observation condition.

14. The sample observation condition setting apparatus according to claim 12, wherein
the processing apparatus is further configured to determine if the electron beam apparatus is capable of the optimum observation condition, and
the electron beam apparatus is further configured to move to another evaluation location including a hole pattern of the sample, to charge the another evaluation location by electron beam irradiation using the optimum observation condition, and to acquire another profile at the another evaluation location when the processing apparatus determines that the electron beam apparatus is capable of the optimum observation condition.

15. The sample observation condition setting apparatus according to claim 9, wherein the hole pattern has a high aspect ratio, and
the electron beam apparatus is configured to acquire a profile of the bottom part after charging.

16. A sample observation apparatus for observing a sample, comprising:
a profile acquisition unit for positively charging an evaluation location including a hole pattern of a sample by electron beam irradiation using a reference observation condition and for acquiring a profile of the hole pattern of the sample; and
a processor configured to determine if a signal amount of the acquired profile corresponding to a bottom part of the hole pattern is within a predetermined range, which is selected to avoid dielectric breakdown due to charging by the electron beam apparatus,
wherein the processor is configured to set an optimum observation condition for the profile acquisition unit based on a result of the determination, and
the optimum observation condition includes a beam irradiation condition of the profile acquisition unit for charging the sample.

17. The sample observation condition setting method according to claim 1,
wherein when said signal amount is determined to be outside of the predetermined range, the third step includes:
setting the optimum observation condition such that an amount of surface charge of the sample after irradiation by the electron beam apparatus using the beam irradiation condition of the optimum observation condition is changed as compared to a surface charge amount after irradiation by the electron beam apparatus using the reference observation condition in the first step, and
determining if the electron beam apparatus is capable of the optimum observation condition; and
when it is determined that the electron beam apparatus is capable of the optimum observation condition, further comprising:
moving to another evaluation location including a hole pattern of the sample; and
repeating said first through third steps at the another evaluation location,
wherein the repeated first step uses the optimum observation condition.

18. The sample observation condition setting method according to claim 1, further comprising:
prior to the positively charging the evaluation location in the first step, acquiring a reference profile at the evaluation location including said hole pattern.

19. The sample observation condition setting method according to claim 18, wherein the second step includes comparing the signal amount of the profile acquired by the first step to a signal amount of said reference profile corresponding to said hole pattern.

20. The sample observation condition setting method according to claim 18, wherein
the acquiring the reference profile and the acquiring the profile in the first step are performed at a same magnification of the electron beam apparatus, and
the positively charging in the first step is performed at a different magnification of the electron beam apparatus from a magnification of the electron beam apparatus in the acquiring the profile in the first step.

* * * * *